United States Patent [19]

Schmitt

[11] Patent Number: 4,536,326

[45] Date of Patent: Aug. 20, 1985

[54] TREATMENT OF ACRYLAMIDE AND RELATED COMPOUNDS

[75] Inventor: Joseph M. Schmitt, Ridgefield, Conn.

[73] Assignee: American Cyanamid Company, Stamford, Conn.

[21] Appl. No.: 570,403

[22] Filed: Jan. 4, 1984

Related U.S. Application Data

[63] Continuation of Ser. No. 362,351, Mar. 26, 1982, abandoned, which is a continuation-in-part of Ser. No. 258,235, Apr. 27, 1981, abandoned.

[51] Int. Cl.$^3$ .................. C09K 15/32; C08F 20/56; C08F 20/06

[52] U.S. Cl. ........................ 252/400 R; 526/303.1; 526/317; 562/598; 564/204

[58] Field of Search ............... 526/77; 252/397, 400.4; 562/600, 598; 564/206, 204

[56] References Cited

U.S. PATENT DOCUMENTS 3,951,600  4/1976  Asano .................................. 422/41

Primary Examiner—Christopher A. Henderson
Attorney, Agent, or Firm—Frank M. Van Riet

[57] ABSTRACT

Acrylamide and related monomers are improved by incorporating therein an effective polymerization inhibitor in an amount greater than that which is inherently present in the monomer and a borane, i.e., sodium borohydride.

12 Claims, No Drawings

TREATMENT OF ACRYLAMIDE AND RELATED COMPOUNDS

CROSS-REFERENCE TO RELATED APPLICATIONS

This application is a continuation of application Ser. No. 362,351, filed Mar. 26, 1982, now abandoned, which is in turn a continuation-in-part of application Ser. No. 258,235 filed on Apr. 27, 1981, now abandoned.

This invention relates to the treatment of acrylamide and related monomers so as to be able to produce water-soluble high molecular weight synthetic polymers, especially when the monomers contain an unacceptably high level of impurities which result in poor polymer products having, for example, excessive amounts of insolubles and/or unacceptably low viscosities and/or low rates of polymerization. More specifically, it relates to the use of a borane compound which contains at least one —B—H moiety to treat acrylamide and/or acrylic acid to produce polymers of acrylamide and/or acrylic acid which are essentially the same as those polymers prepared from especially pure monomers.

Acrylamide is conventionally prepared by the hydration of acrylonitrile as is well-known. This material generally exits the process as a concentrated (30 to 60% by weight) aqueous solution. Acrylic acid is conventionally prepared by the oxidation of propylene as is well-known in the art. This material generally is available as concentrated aqueous solutions, i.e., 60% to glacial. For economical reasons, it is extremely desirable that these products be directly polymerized to water-soluble, high molecular weight polymers. However, these monomer solutions or powders apparently contain unknown impurities at the level of parts per million, the exact amount or type being undetermined to date. When such monomers are polymerized, even with this very low level of impurities present, quite often totally unacceptable polymers result.

In solution polymerizations, attempts at solving these problems required any or all of: (a) very low polymer drying temperature; (b) extensive and expensive purification of the monomer solution by recrystallization; (c) very long polymerization times; (d) addition of very large amounts of urea or chain transfer agents to the monomer; (e) polymerizing in very dilute solutions and (f) adding post-polymerization stabilizers. However, each of these has been found unsatisfactory for large scale commercial use due to being either energy-intensive or expensive in that the rate of production of polymers is drastically curtailed or the percent of desirable polymer is reduced to an unacceptable level.

In water-in-oil emulsions, attempts at solving these problems entailed: (a) monomer purification by recrystallization; (b) polymerizing very dilute solutions; (c) use of different initiators; (d) addition of urea to the monomer; and/or (e) use of chain transfer agents. However, these have also been found unsatisfactory for the same or similar reasons as above.

In U.S. Pat. No. 2,963,459 there is disclosed the use of metal borohydrides as catalysts for aqueous emulsion polymerization. Defensive Publication T875,006 discloses the use of alkali metal and alkaline earth metal borohydrides as catalysts to control the steric configuration and physical properties in the bulk or solution polymerization of acrylic monomers.

Accordingly, developments that could purify impure monomers readily and result in polymers therefrom of greater molecular weight or viscosity with minimum amounts of insolubles therein would fulfill a long known need and constitute a notable advance in the art.

In accordance with the present invention, there is provided a composition comprising (a) a monomer of inferior polymerizability selected from acrylamide, acrylic acid and mixtures thereof, (b) an effective polymerization inhibitor in an amount greater than that which is inherently present in said monomer and (c) a borane compound containing at least one —B—H moiety selected from borohydrides and complexes of boron hydrides, optionally on a resinous support.

There is also provided a method for improving the polymerizability of a monomer of inferior polymerizability selected from acrylamide, acrylic acid and mixtures thereof comprising treating said monomer in the presence of an effective polymerization inhibitor in an amount sufficient to inhibit polymerization with an effective amount of a borane compound having at least one —B—H moiety selected from borohydrides and complexes of boron hydrides for a sufficient time to provide a monomer of improved polymerizability.

There is still further provided a process for producing a water-soluble high molecular weight polymer by polymerizing a monomer selected from acrylamide, acrylic acid and mixtures thereof characterized by treating said monomer in the presence of an effective polymerization inhibitor in an amount sufficient to inhibit polymerization with an effective amount of a borane compound having at least one —B—H moiety selected from borohydrides and complexes of boron hydrides for a sufficient time to provide a monomer of improved polymerizability prior to polymerization.

In accordance with the present invention, the borane treatment of monomers of inferior polymerizability enables polymers to be provided that have higher viscosities and lower amounts of insolubles than corresponding polymers made from untreated monomers of inferior polymerizability.

By the expression "improving the polymerizability of a monomer of inferior polymerizability, as that term is used herein and in the appended claims, is meant providing a monomer which produces a polymer of higher molecular weight as indicated by standard viscosity than does the corresponding monomer of inferior polymerizability, produces a polymer containing less insolubles than does the corresponding monomer of inferior polymerizability or provides both higher viscosity and lower insolubles.

The compounds used herein to produce improved acrylamide and/or acrylic acid are those compounds which contain at least one —B—H moiety. These compounds are referred to as boranes. Generally, these compounds have been known to be catalysts or parts of catalyst systems for the polymerization of acrylamide and/or acrylic acid but under the controlled conditions herein, they do not cause such polymerization.

These compounds may be borohydrides or complexes of boron hydrides with other compounds.

Examples of borohydrides useful herein include, but are not limited to: the borohydrides (tetrahydroborates) of sodium, potassium, rubidium, cesium, calcium, barium, strontium, magnesium, thorium, mercury, gold and lead; the cyanoborohydrides of the above metals; Lalancette's Reagent (NaBH$_2$S$_3$); hydridotrialkoxyborates of the above metals; tetramethyl ammonium octahydrotriborate as well as other hydropolyborates, e.g. salts of $B_{12}H_{12}^{-2}$; and the like. Preferably, the alkali metal borohydrides are used. Most preferably, sodium borohydride is used due to its commercial availability.

Examples of complexes of boron hydrides with other compounds include the amine boranes wherein amines are combined with tetrahydroborates. Suitable such amines include ammonia, methylamine, dimethylamine, trimethylamine, triethylamine, isopropylamine, t-butylamine, N,N-dimethyl-2-methoxyethylamine, pyridine, piperazine, morpholine, methylmorpholine, 2,6-lutidine, methoxypyridine, 4-aminopyridine and the like.

Alternatively, the borane compound may be supported on resin or used as a counterion on a quaternary ion exchange resin or as in commercially available Amborane ® resins of Rohm and Haas, or amine polymers which are reacted with borohydrides, e.g. poly(4-vinylpyridine)borane.

Any borane compound to be useful herein must, of course, have sufficient stability in the monomer to overcome the detrimental effects of the impurities prior to decomposition.

The acrylamide and acrylic acid used herein are any which are conventionally prepared or sold and have inferior polymerizability. Generally they contain metallic ions such as cuprous, cupric, ferrous and ferric or other compounds which might potentially form an initiator system in the presence of the borane. The metallic ions may either be present due to the manufacture of the monomer or due to being intentionally added to inhibit polymerization or for some other purpose such as color reversion. Alternatively, the monomers may have been pretreated to remove the metallic ions or compounds or to greatly reduce their amount in the monomer.

To perform the treatment herein and incorporate the borane compound into the monomer, a sufficient amount of an effective polymerization inhibitor greater than that which is inherently present in the monomer and the borane are added. The most convenient polymerization inhibitor to use is oxygen and it may be provided by means of an air or oxygen sparge. The amount of oxygen to be used is such as to maintain a positive oxygen solubility in the monomer during the entire treatment. This should be at least about 0.1 part per million, preferably at least 1 part per million and most preferably at least 2 parts per million. Other suitable inhibitors include such as hydroquinone, monomethyl ether of hydroquinone and such other well-known analogs, catechol, tertiary-butyl catechol, resorcinol, eugenol and the like, as well as phenylthiazine.

For the use of sodium borohydride, the pH during at least a portion of the treatment should be above 8 and preferably above 10. These pH values may be obtained by the addition of a base such as caustic to the monomer or by merely increasing the amount of sodium borohydride being used as it is itself very basic.

The amount of borane compound to be used in accordance with the present invention has been found to depend, at least in part, upon the type of polymerization the monomer may subsequently undergo, the pH of the monomer being treated, the amount of impurities in the monomer being treated, the presence or absence of urea during the polymerization and the amount thereof, and the time allowed for the treatment, as well as the concentration of the monomer solution being treated. As such, an exact "monomer improving amount" cannot be defined. Generally, however, it may range from about 50 parts per million to about 2 weight percent, preferably from about 50 to 5000 parts per million based upon the monomer. When the monomer is to be used for water-in-oil emulsion polymerizations, which are generally performed at higher solids levels, generally larger amounts of the borane should be used, the smaller amounts have been found to suffice for solution polymerizations. Most preferably about 100 to 2,000 parts per million are used.

Generally the treatment time may be from minutes to hours, with the time a function of the amount of borane used. Thus, suitable treatment times may range from about 5 minutes to 8 hours. A treatment time of about 1 to 3 hours with a borane content of about 200 parts per million on a 50% by weight acrylamide solution has been found suitable for making a solution polymerized polyacrylamide.

After the treatment, any excess borane compound may be removed by passing the monomer solution through a column which will attract the borane compound or, preferably, it may be decomposed to the corresponding borate by the addition of an acid. This reaction liberates hydrogen and hence should be done with proper safety precautions. Thus, the use of dilute acids for relatively extended times are preferred. Suitable acids include sulfuric, phosphoric, hydrochloric and the like. They should be used at about 5 to 20 weight percent solutions with the addition taking from at least 15 minutes, preferably about 30 minutes, up to about an hour. Although shorter times and higher concentrations may be used, there is an increased risk of unwanted, uncontrolled premature polymerization of the polymer. During the acidification, the hydrogen gas content of the air should be maintained at below 4%. Alternatively, an extended treatment time of up to several days without acidification may be allowed for the borane to slowly hydrolyze to the corresponding borate.

The process of treating the impure monomer may be conducted in continuous manner, if desired. In such procedure, the monomer in solution form is fed to a first reactor along with suitable treating agent while sparging with air. The solution plus treating agent overflow the first reactor and enter a second reactor wherein sparging continues. Suitable flow rates are employed in the two reactors in conjunction with stirring so as to provide adequate residence time for complete reaction. The solution is then transferred to a third vessel where it is treated with acid with stirring and sparging continuing so as to decompose excess treating agent.

Even following the above borane treatment, it has sometimes been found advantageous to incorporate into the polymerization recipe up to about 20 weight percent based upon monomer of urea or a urea derivative. Generally, 5 to 10 weight percent of urea itself is used. Suitable such compounds are disclosed in U.S. Pat. No. 3,622,533.

Copolymers of the above named monomers or of one or more of the named monomers with other ethylenically unsaturated monomers suitable to produce water-soluble products may also be prepared. Such other monomers include, but are not limited to, methacrylamide, salts of acrylic acid, methacrylic acid and the salts, methyl acrylate, ethyl acrylate, propyl acrylate, methyl methacrylate, ethyl methacrylate, dimethylaminoethylacrylate, diethylaminoethylacrylate, diethylaminoethyl methacrylate, hydroxyethyl acrylate, hydroxyethylmethacrylate, diethylaminoethyl acrylate methylsulfate quaternary salt, styrene, acrylonitrile, 3-(methacrylamido)propyl-trimethylammonium chloride, vinyl methyl ether, vinyl ethyl ether, alkali metal and ammonium salts of vinyl sulfonic acid, and the like. All or part of the acrylamide portion of the polymers may be hydrolyzed.

The polymerization process to be used with the treated monomer is any which is conventionally used to polymerize such monomers. This specifically includes solution and emulsion polymerizations, although other techniques such as bead and suspension or dispersion polymerizations may be used. The particular polymerization system for each of these is that which is conventionally used. For solution polymerization this generally entails using one or more azo-initiators with or without a redox system, and optionally such conventional additives as sequesterants, alcohols and diluents as necessary to the polymerization. For emulsion polymerization, which is a water-in-oil emulsion, this entails using a water-in-oil emulsifying agent, an oil phase such as toluene, xylene or a paraffinic oil, and a free radical initiator.

As the present invention is independent of the particular polymerization method, further details on polymerization may be found in the literature. Furthermore, the quantities and the individual components will vary according to the monomers polymerized and the process conditions under which the polymerization is to occur.

The following specific examples illustrate certain aspects of the present invention and more particularly point out the benefits obtained thereby. However, the examples are set forth for illustration only and are not to be construed as limitations on the present invention except as set forth in the appended claims. All parts and percentages are by weight unless otherwise specified.

EXAMPLE 1

Treatment of Acrylamide with $NaBH_4$

A. To a glass beaker are added 500 grams of 50% aqueous acrylamide "as is" which contained about 25 ppm copper based on the acrylamide and other conventional impurities found in acrylamide. An air sparge is started at the rate of 750 ml per minute and continued during the entire treatment. The pH is raised to 10 by the addition of an appropriate amount of 50% aqueous sodium hydroxide. Thereafter 0.1 g (200 ppm) of sodium borohydride in the form of a 2.5% aqueous solution is added and the mixture is stirred to ensure rapid dispersion of the sodium borohydride. After two hours, the remaining sodium borohydride is hydrolyzed to sodium metaborate by the addition of a 5% aqueous $H_3PO_4$ over a period of about 30 minutes.

B. When the above procedure is repeated in the absence of an air sparge, polymerization of the acrylamide occurs shortly after the addition of the sodium borohydride.

EXAMPLE 2

The procedure of Example 1a is repeated except that variations are made in (1) the borohydride concentration, (2) the copper content, (3) the amount of air, (4) the hydrolysis conditions, and (5) the pH of the acrylamide when the borohydride is added.

The results are in Table I below wherein it can be seen that with the higher levels of copper present, the more air is needed and the slower the hydrolysis must be to prevent premature polymerization. Also, at the more rapid hydrolysis conditions, the greater is the likelihood of premature polymerization. In the table, "added rapidly" means within about one minute, "0" means no premature polymerization occurred and "+" means that there was premature polymerization.

TABLE I

| | Polymerization During Treatment with Sodium Borohydride | | | |
|---|---|---|---|---|
| $NaBH_4$ ppm/AMD | Cu ppm/AMD | Air Rate Vol/Vol Sol'n-Min | Hydrolysis Condition | Premature Polymerization |
| | | Treating 50% Acrylamide Solutions | | |
| 2000 | 25 | 1.5 | 25% $H_2SO_4$ added rapidly | 0 |
| 1000 | 25 | 1.5 | 25% $H_2SO_4$ added rapidly | 0 |
| 500 | 25 | 1.5 | 25% $H_2SO_4$ added rapidly | 0 |
| 200 | 25 | 1.5 | 25% $H_2SO_4$ added rapidly | + |
| 200 | 25 | 1.5 | 2.5% $H_2SO_4$ added rapidly | + |
| 100 | 25 | 1.5 | 2.5% $H_2SO_4$ added rapidly | + |
| 100 | 25 | 1.5 | 2.5% $H_2SO_4$ added rapidly | 0 |
| 50 | 25 | 1.5 | 25% $H_2SO_4$ added rapidly | 0 |
| 50 | 25 | 1.5 | Solution pH 5.3 when $NaBH_4$ added, immediate polymerization | + |
| 50 | 25 | 1.5 | Solution pH 9 when $NaBH_4$ added, 25% $H_2SO_4$ added rapidly | 0 |
| | | Treating 25% Acrylamide Solutions | | |
| 200 | 0.1 | 0.07 | 5% $H_3PO_4$ over 30 min. | 0 |
| 200 | 0.1 | 0.07 | 85% $H_3PO_4$ rapidly-no stirring | 0 |
| 200 | 0.1 | 0.07 | 85% $H_3PO_4$ rapidly-with stirring | 0 |
| 200 | 22.0 | 0.07 | 85% $H_3PO_4$ rapidly-with stirring | + |
| 200 | 22.0 | 0.07 | 5% $H_3PO_4$ over 30 min. | + |
| 200 | 2.3 | 0.07 | 5% $H_3PO_4$ over 30 min. | + |
| 200 | 0.5 | 0.07 | 5% $H_3PO_4$ over 30 min. | 0 |
| 200 | 1.0 | 0.07 | 5% $H_3PO_4$ over 30 min. | 0 |
| 200 | 1.9 | 0.07 | 5% $H_3PO_4$ over 30 min. | + |
| 200 | 1.4 | 0.07 | 5% $H_3PO_4$ over 30 min. | 0 |
| 200 | 1.9 | 0.07 | 5% $H_3PO_4$ over Capillary Sparger | 0 |
| 200 | 22.0 | 0.07 | 5% $H_3PO_4$ over Capillary Sparger | + |
| | | Treating 10% Acrylamide Solutions | | |
| 200 | 22.0 | 0.03 | 5% $H_3PO_4$ in 10 min. | + |
| 200 | 22.0 | 0.06 | 5% $H_3PO_4$ in 30 min. | 0 |
| 200 | 3.0 | 0.03 | 5% $H_3PO_4$ in 30 min. | 0 |
| 200 | 3.0 | 0.03 | 5% $H_3PO_4$ rapidly | 0 |

TABLE I-continued

| | | Polymerization During Treatment with Sodium Borohydride | | | |
|---|---|---|---|---|---|
| NaBH4 ppm/AMD | Cu ppm/AMD | Air Rate Vol/Vol Sol'n-Min | Hydrolysis Condition | | Premature Polymerization |
| 200 | 25.0 | 1.5 | 25% H3PO4 rapidly | | 0 |
| 200 | 0.2 | 1.5 | 25% H3PO4 rapidly | | 0 |

EXAMPLE 3

Solution Polymerization of Monomer of Example 1(a)

The monomer solution of Example 1(a) (102.4 g) is solution polymerized as follows: It is placed in a polyethylene reactor and magnetically stirred. The following are subsequently added while the stirring continued:
397.6 g deionized water
1.5 ml 2% aqueous ethylenediamine tetraacetic acid disodium salt
2.1 g anhydrous sodium sulfate
0.51 g anhydrous ammonium sulfate
2.62 g urea When solution is complete, the pH of the reaction mass is adjusted to 4.5 with sulfuric acid. A nitrogen purge is started at about 250 ml/minute and continued for 30 minutes while warming the reaction mass to about 35° C. With the nitrogen purge continuing, polymerization commences within minutes after the introduction of the catalyst:
0.98 ml of 2% aqueous 2,2'-azobis-(2-amidinopropane)dihydrochloride The polymerization is allowed to continue substantially adiabatically by insulating the reactor. The polymerizate is allowed to experience a 23.2° C. exotherm over about a four-hour period prior to being transferred to a curing oven at approximately 65° C. where it cures for an additional 18 hours, producing about 500 grams of a stiff gel product.

The gel is subsequently cut into slivers and portions thereof dried in a convection oven to 7–10% residual volatiles at a temperature of 90° C. The dried product is reduced in particle size in a Waring Blender and screened to yield product at a −20 U.S. mesh particle size.

EXAMPLE 4

Evaluation of Product of Example 3

To evaluate the product prepared in Example 3, the following is done:

0.3 gram of the dried product is dissolved over 2 hours in deionized water to produce 300 grams of about 0.1% aqueous polymer solution. The solution is passed through a 100 U.S. mesh weighed screen to filter out any unsolubles. The screen is washed with about 500 ml deionized water at room temperature and dried at 100° C. overnight to determine the amount of insolubles which is reported as percent insolubles.

The percent residual volatiles is determined by measuring the weight loss of a 1-gram sample after drying at 100°–110° C. overnight.

The extent of hydrolysis (percent carboxyl) is determined by a conductometric titration of the carboxyl content in the polymer. The lower the number reported, the better is the resultant product for nonionics.

The "as is" standard viscosity is determined by dissolving 0.3 gram of product in deionized water over 2 hours to yield a 300 gram aqueous solution, filtering out the insolubles through a 100 U.S. mesh screen, and then adding enough sodium chloride to form a 1 Molar NaCl solution and determining the Brookfield viscosity thereof using a UL (ultra low) adaptor. This is indicative of the performance of the resultant product in that the higher the number, the more desirable is the final product.

The results, along with a comparison product prepared by the same procedure but wherein no borane treatment was used are shown in Table II below. They clearly demonstrate that by pretreating the monomer with 200 ppm sodium borohydride the "as is" viscosity is greatly increased and the percent insolubles is reduced from about 45% to less than 0.1%.

The "as is" viscosity, refers to the weight of polymer used, including salts and volatiles. In certain other standard viscosity determinations, measurements are on a real polymer basis.

TABLE II

| Results of Example 3 and Comparison | | |
|---|---|---|
| | Example 3 | Comparison |
| "As Is" Standard viscosity, cps. | 3.6 | 1.9 |
| % volatiles | 8.5 | 7.3 |
| % insolubles | 0.1 | 45.3 |
| % Carboxyl | 0.33 | — |

EXAMPLE 5

The procedures of Examples 3 and 4 are repeated on a different acrylamide monomer, varying the amount of sodium borohydride and the pH when the borohydride is added.

The results are:

| NaBH4 ppm | Initial pH | Time min. | "As Is" Standard Viscosity cps | % Insolubles |
|---|---|---|---|---|
| 0 | — | — | 1.9 | 45.0 |
| 50 | 10 | 120 | 3.0 | 7.6 |
| 50 | 11 | 120 | 3.2 | 12.0 |
| 100 | 10 | 120 | 3.7 | 2.0 |
| 100 | 11 | 120 | 3.7 | 4.9 |
| 200 | 11 | 120 | 3.6 | 0.1 |

The results demonstrate that as the amount of borohydride is increased, the % insolubles decreases and the viscosity increases. Moreover, when the amount of borohydride is 200 ppm, a two hour treatment time was sufficient to bring the insolubles content to below 2.0%.

EXAMPLE 6

The procedure of 1(a), 3 and 4 are repeated except that the acrylamide is treated as a 25% solution with 200 ppm NaBH4 at a pH of 10 for two hours. The residual NaBH4 is decomposed with a 5% aqueous phosphoric acid solution utilizing a 30 minute addition period to minimize hydrogen content in the reactor exhaust streams.

The results of three separate polymerizations of this monomer are:

| Polymerization | "As Is" Standard Viscosity, cps. | % Insolubles |
| --- | --- | --- |
| A | 3.8 | 0.8 |
| B | 3.9 | 0.7 |
| C | 4.0 | 0.6 |

EXAMPLE 7

An acrylamide monomer solution is solution polymerized as follows: 240.4 g of a 49.92% aqueous acrylamide solution is placed in a reactor and mechanically stirred. The following are subsequently added while the stirring continues:
 199.6 g deionized water
 1.1 g anhydrous ammonium chloride
 6.0 g urea
 3.9 g methanol
 0.9 ml 5% aqueous diethylenetriaminepentaacetic acid When solution is complete, the pH of the reaction mass is adjusted to 6.0 with hydrochloric acid. The system is then cooled to about −70° C. by a dry ice bath and purged with nitrogen by means of a sparge at about 500 ml per hour for 30 minutes while maintaining the temperature below about 0° C. With the nitrogen purge continuing, the reactor is removed from the ice bath and polymerization commences within minutes after the introduction of the catalyst system:
 1.1 ml 0.3% aqueous ferrous ammonium sulfate
 4.4 ml 0.1 g ammonium persulfate plus 7.5 g 2,2′-azobis(2-amidinopropane)-dihydrochloride in 100 ml water The reactor is capped, the $N_2$ sparge stopped and the polymerization is allowed to continue substantially adiabatically. The temperature rises to about 72° C. over about 95 minutes and the solution is allowed to stand overnight at room temperature producing about 440 grams of a stiff gel product.

The gel is subsequently cut into slivers, extruded and dried at 90° C. for 2 hours. The dried product is reduced in size in a Waring Blender and screened to yield a product at a −20 U.S. mesh particle size.

The above polymerization is performed on an untreated acrylamide polymer. The procedure is then repeated using sodium borohydride treated acrylamide prepared as in Example 1(a) as shown in Table III below, wherein the properties of each polymer are also reported.

TABLE III

| $NaBH_4$/AMD ppm | Initial pH | Treatment Time, min. | Standard Viscosity cps | % Insolubles |
| --- | --- | --- | --- | --- |
| 0 | — | — | 2.4 | 28.7 |
| 50 | 9.0 | 120 | 2.5 | 28.7 |
| 50 | 9.0 | 120 | 2.4 | 33.5 |
| 200 | 5.5 | 120 | 1.5 | 53.4 |
| 200 | 9.0 | 120 | 4.1 | 1.2 |
| 500 | 5.5 | 120 | 4.0 | 0.6 |
| 500 | 9.0 | 120 | 4.4 | 0.1 |
| 1000 | 5.5 | 10 | 3.9 | 6.2 |
| 1000 | 5.5 | 20 | 4.3 | 0.5 |
| 1000 | 5.5 | 30 | 4.4 | 0.4 |

EXAMPLE 8

The procedure of Example 7 is repeated except that the amount of sodium borohydride is increased to 2000 ppm and the pH and treatment time are varied. The results are:

| $NaBH_4$/AMD ppm | Initial pH | Time min. | Standard Viscosity, cps | % Insolubles |
| --- | --- | --- | --- | --- |
| 0 | — | — | 2.4 | 28.7 |
| 2000 | 5.3 | 5 | 4.1 | 0.7 |
| 2000 | 8.4 | 5 | 3.4 | 18.1 |
| 2000 | 8.1 | 60 | 4.5 | 1.3 |

EXAMPLE 9

To determine the long-term stability of polymer prepared after treatment of the monomer with sodium borohydride, samples of the monomer are treated under varying conditions and polymerized in accordance with the procedure of Example 7. The properties of the polymers after the specified storage times are given in Table IV. They show excellent storage stability of the polyacrylamides made from the treated monomers.

TABLE IV

Stability of Polymer from Treated Acrylamide, Treatment Conditions

| Days of Storage | Initial pH | ppm $NaBH_4$ | Time hrs. | Standard Viscosity CPS | % Insolubles | % Carboxyl Content |
| --- | --- | --- | --- | --- | --- | --- |
| 0 | 5.2 | 2000 | 1 | 4.5 | 1.3 | |
| 56 | | | | | | 0.47 |
| 71 | | | | 4.5 | 1.7 | |
| 136 | | | | 4.2 | 0.8 | |
| 150 | | | | | | 0.63 |
| 0 | 5.2 | 1000 | 0.5 | 4.4 | 0.4 | |
| 28 | | | | | | 0.62 |
| 87 | | | | 4.0 | 0.1 | |
| 108 | | | | 4.2 | 0.5 | |
| 122 | | | | | | 0.56 |
| 0 | 9 | 500 | 2 | 4.4 | 0.1 | |
| 28 | | | | | | 0.35 |
| 58 | | | | 4.2 | 0.8 | |
| 92 | | | | 4.1 | 0.2 | |
| 117 | | | | | | 0.38 |
| 0 | 9 | 200 | 2 | 4.3 | 1.2 | |
| 28 | | | | | | 0.43 |
| 58 | | | | 4.1 | 2.4 | |
| 92 | | | | 4.1 | 1.2 | |
| 117 | | | | | | 0.48 |

EXAMPLE 10

To determine the long-term stability of monomer which is treated with sodium borohydride many days prior to polymerization, a sample of acrylamide is treated with two different amounts of borohydride for different times in separate runs. Thereafter the monomers are stored until they are eventually polymerized in accordance with the procedure of Example 3. The treatment conditions and results are:

| $NaBH_4$/AMD ppm | Initial pH | Time min. | Time Stored | "As is" Standard Viscosity cps | % Insolubles |
| --- | --- | --- | --- | --- | --- |
| — | — | — | — | 1.9 | 45.0 |
| 1000 | 5.2 | 30 | 53 | 3.7 | 5.5 |
| 2000 | 5.2 | 60 | 93 | 3.7 | 0.3 |

EXAMPLE 11

Emulsion Polymerization of Acrylamide

Acrylamide is treated as in Example 1(a) with varying amounts of sodium borohydride and for varying treatment times as shown in Table V below. These monomers are then polymerized by a water-in-oil emulsion procedure according to the following description.

To a suitable reaction vessel are added 378.4 parts of acrylamide as a 51.08% aqueous solution and 111.6 parts of deionized water. To this solution are added 6.9 parts of a 5.6% aqueous solution of the disodium salt of ethylenediamine tetraacetic acid and 1 part of 1.4% aqueous solution of t-butyl hydroperoxide. The pH of the resultant solution is adjusted to 5.0. This constitutes the aqueous monomer phase.

The oil phase is prepared by dissolving 15.0 parts of sorbitan monooleate in 179.2 parts of Exxon LOPS, a commercially available, clear oily liquid sold by Exxon Chemical.

To a suitable, high-speed homogenizer is added the complete oil phase system. The homogenizer is started and the monomer aqueous phase is slowly added thereto to form an emulsion having a viscosity of 1500 cps. The dispersed phase of the resultant emulsion has a particle size of about 2.5 microns or less.

To a suitable reaction vessel is added the complete emulsion system with stirring. The resulting media is purged with nitrogen gas. Stirring continues and sodium metabisulfite is slowly pumped into the vessel over a period of six hours while maintaining the vessel at about 40° C. after which about 100 parts per million (based on monomer) have been added. The resultant viscous emulsion exhibits 99.49% conversion of acrylamide.

Stabilization of the polymer emulsion is accomplished by adding 13.5 parts of a 30% aqueous sodium metabisulfite solution. The emulsion is maintained under polymerizing conditions (60 minutes at 40° C.) to substantially completely react the remaining acrylamide. 0.4% of the emulsion comprises free bisulfite which effects stabilization of the polymer system.

To the resultant polymer is added, as an inverting agent mixture over a period of about 30 minutes, the reaction product of a $C_{12}$-$C_{14}$ alcohol and ethylene oxide (Alfonic 1412-60) in an amount so as to be 2.1% based on the total finished emulsion. The resultant emulsion is stirred at 40° C. for an additional hour after which time the product is smooth and particle free. The dispersed polymer phase has a particle size of 2.5 microns or less.

The standard viscosity of the resultant product, as well as those other products prepared by varying the amount of sodium borohydride and the treatment times, are shown in Table V below. As different samples of acrylamide monomer are used for each series, there are three separate controls provided.

TABLE V

| | Results of Emulsion Polymerization | | |
|---|---|---|---|
| $NaBH_4$/AMD | Treatment Conditions | | Standard |
| ppm | pH | Time, hrs | Viscosity cps |
| — | — | — | 2.7 |
| 1000 | 10.0 | 2 | 4.4 |
| 2000 | 10.0 | 2 | 4.3 |
| — | — | — | 3.6 |
| 500 | 10.0 | 2 | 4.8 |
| 1000 | 10.0 | 2 | 4.5 |
| 2000 | 10.0 | 2 | 4.5 |
| — | — | — | 4.1 |
| 500 | 10.0 | 4.5 | 5.0 |
| 2000 | 10.0 | 2 | 5.2 |

EXAMPLE 12

Preparation of Copolymers

The basic procedure of Example 3 is repeated except that 10% by weight of the acrylamide is replaced in separate runs by an equivalent weight of each of the following monomers:
(a) acrylic acid
(b) 2-acrylamido-2-methylpropane ammonium sulfonate
(c) Dimethylaminoethylmethacrylate methyl sulfate quaternary salt For (a) and (b) the pH is adjusted with ammonium hydroxide.

Comparable improved results over those same copolymers prepared from untreated acrylamide are observed.

EXAMPLE 13

Use of Other Borohydrides

The procedure of Examples 1(a) and 3 is repeated except that the sodium borohydride is replaced by the following compounds:
Sodium cyanoborohydride
Potassium borohydride Similar improved results are observed with these compounds.

EXAMPLE 14

The procedure of Example 3 is repeated except for varying the presence of urea and the amount of sodium borohydride used. All treatments are for 2 hours at pH 10. The data in Table VI below demonstrates that when 5% urea is included in the subsequent polymerization recipe, the amount of borohydride needed to treat the monomer is greatly reduced.

TABLE VI

| | Results of Example 14 | | |
|---|---|---|---|
| $NaBH_4$/AMD ppm | Urea | "As Is" Standard Viscosity, cps. | % Insolubles |
| — | Yes | 3.3 | 8.8 |
| 200 | Yes | 4.0 | 0.3 |
| 200 | No | 1.7 | 45.5 |
| 500 | No | 3.2 | 14.8 |
| 1000 | No | 3.4 | 7.0 |
| 2000 | No | 3.6 | 3.5 |
| 2000 | Yes | 3.8 | 0.2 |

EXAMPLE 15

Hydrolyzed Polyacrylamide Products

The procedure of Example 3 is repeated with the following variations: (1) the monomer content is increased to about 12%; (2) the pH of the polymerization is raised to 6.0; and (3) the urea and ammonium sulfate are replaced by equal weights of sodium sulfate.

The monomer used is treated as in Example 1(a) with 200 ppm sodium borohydride for 2 hours at pH 10.

After the polymeric gel is prepared, it is treated with various amounts of caustic for about 15 minutes and optionally various post-additives to improve its stability. The various runs and results are as shown in Table VII below.

TABLE VII

| | Results of Example 15 | | | | | |
|---|---|---|---|---|---|---|
| | Control | NaBH$_4$ Treated | Control | NaBH$_4$ Treated | Control | NaBH$_4$ Treated |
| NaOH level, % | 8 | 8 | 30 | 30 | 30 | 30 |
| Post additives, % | | | | | | |
| Sodium metabisulfite | 1.2 | 1.2 | — | — | — | — |
| Sodium thiocyanate | 1.3 | 1.3 | — | — | — | — |
| Thiourea | — | — | — | — | 1.0 | 1.0 |
| "As is" viscosity, cps | 2.1 | 4.5 | 4.3 | 5.4 | 4.9 | 5.3 |
| % Insolubles | WNF | 2.5 | WNF | 0.1 | 3.8 | 0.2 |

WNF MEANS WILL NOT FILTER

EXAMPLE 16

Cationic Solution Polymer

A. NaBH$_4$ Treatment of Acrylamide

To a suitable vessel equipped with stirrer and gas purge tube are added 468.2 grams of a 50.53% aqueous solution of an impure acrylamide free of cupric ion and the pH is adjusted to 10 with 10% aqueous NaOH. While purging with air at the rate of 750 millileters per minute (air flow) and stirring, 20 ml. of a 2.5% aqueous solution of NaBH$_4$ is added slowly so as to provide about 2000 parts of NaBH$_4$ per million parts of acrylamide. To 2.5% solution of NaBH$_4$ is prepared by adding the NaBH$_4$ powder to water adjusted to pH 13 with NaOH. After 2 hours of continued stirring and air purging, the pH of the acrylamide solution is adjusted to 5.4 by slowly adding 31 ml. of 0.5N H$_2$SO$_4$ to decompose the excess NaBH$_4$.

B. Polymer Preparation

To 236.2 grams (46.62% acrylamide) of the accrylamide of part A are added 94.4 grams of an 82% aqueous solution of the methyl sulfate quaternary of dimethylaminoethylmethacrylate, 148.4 grams deionized water, 10 ml. of a solution of 0.8 gram of azobisisobutyronitrile and 31.6 g of methyl alcohol, and 1 ml of an aqueous solution of 3.29 grams of ZuSO$_4$.7H$_2$O, 0.84 gram of ethylene-diaminetetraacetic acid disodium salt dihydrate and 95.87 grams of deionized water. The pH is adjusted to 4.0 with a few drops of 0.5N H$_2$SO$_4$. The monomer content is about 37%.

The solution is cooled to about −5° C. and added to a Dewar flask equipped with gas purge tube, gas exit tube, thermocouple, injection port and magnetic stirrer. With the stirrer on, the solution is purged with nitrogen for 0.5 hour at 350 ml/min gas flow after which the temperature of the ingredients is about 0° C. With continued stirring and purging, 5 ml of a 0.1% aqueous solution of ammonium persulfate followed by 5 ml. of a 0.18% aqueous solution of ferrous ammonium sulfate hexahydrate are added. After 2 min. the purge tube is moved to the vapor space in the Dewar. When the temperature reaches 50° C., the stirrer and nitrogen are shut off. The total exotherm is 73.5° C. After which the Dewar is allowed to stand for 20 hours unopened at room temperature.

The resulting polymer gel is dried at 85° C. for 2 hours in a forced draft oven to a volatile content of 4.43%, ground and sieved through a 30 mesh screen (U.S. Standard). The standard viscosity of the polymer is 3.2 centipoises and insolubles are 0.18%. In a control run wherein the acrylamide is not treated with NaBH$_4$, the polymer has a viscosity of 3.5 centipoises and insolubles of 35.6%.

EXAMPLE 17

The procedure of Example 16 is followed with the following exceptions.

Two alternative sources of acrylamide are employed. Source A provides an impure acrylamide which is freed of cupric ion by ion exchange. Source B also provides an impure acrylamide which is freed of cupric ion by ion exchange. These acrylamides are divided into portions, one portion being treated as in Example 16, part A and the second portion being untreated.

Following polymerization and drying as in Example 16, part B, the following results are obtained in two separate runs employing each acrylamide source.

| Acrylamide Source | NaBH$_4$ Treated | Polymer Solids % | Induction Time | T. Maximum Temp | T. Maximum Time | % Insolubles |
|---|---|---|---|---|---|---|
| A | No | 37.5 | Would Not Polymerize | | | — |
| A | Yes | 37.5 | 4 | 74° C. | 182 Min | >50 |
| B | No | 37.5 | 53 | 76° C. | 298 Min | >50 |
| B | Yes | 37.5 | 3 | 76° C. | 174 Min | 0.0 |
| A | No | 37.5 | 26 | 74° C. | 197 Min | Would not Filter |
| A | Yes | 37.5 | 24 | 68° C. | 282 Min | 20.1 |
| B | No | 37.5 | 40 | 78° C. | 267 Min | 35.6 |
| B | Yes | 37.5 | 8 | 76° C. | 191 Min | 0.2 |

EXAMPLE 18

Emulsion Polymerization

A. NaBH$_4$ Treatment of Acrylamide and Acrylic Acid

To a suitable vessel equipped with a stirrer and gas purge tube are added:

205.4 grams (104.8 grams real) acrylamide as 51.02% aqueous solution and free of cupric ion and 45.5 grams acrylic acid The acid solution is adjusted with 83.8 grams of 25% aqueous NaOH to pH 10.0 while keeping the temperature below 40° C. While purging the monomer solution with 400 ml/min. of air, 12 ml. of a 2.5% aqueous solution of NaBH$_4$ is added slowly to provide about 2000 parts NaBH$_4$ per million parts of total monomers. The NaBH$_4$ solution is prepared by adding crystaline NaBH$_4$ to deionized water at pH13 with NaOH. After 2 hours of continued stirring and air purging, the pH of the monomer solution is adjusted to 6.0 by adding slowly 16 mls of 5N H$_2$SO$_4$ to decompose excess NaBH$_4$.

B. Emulsion Preparation and Polymerization

To the monomer solution obtained from A above are added 5.36 ml of a 5.6% aqueous solution of the disodium salt of ethylenediamine tetraacetic acid, 6.9 grams of 30% NH₄OH to give a pH of about 7.5 and enough deionized water to give a total aqueous phase of 410.6 grams.

The oil phase is prepared by dissolving 11.4 grams of sorbitan monooleate in 145.3 grams of Exxon LOPS, a commercially available clear oily liquid sold by the Exxon Co.

To a suitable high speed homogenizer is added the complete oil phase system. The homogenizer is started and the monomer aqueous phase is slowly added to form an emulsion having a viscosity of 700 centipoises.

To a suitable reaction vessel is added the complete emulsion system with stirring. 1 ml of 1.05% t-butyl peroxide is added. The resultant medium is purged with nitrogen gas to remove oxygen from the system. Stirring continues and sodium metabisulfite is slowly pumped into the vessel over a period of about 4.5 hours during which time the polymerization exotherm increases the reaction temperature from about 25° C. to 50° C. in about 0.5 hour. The temperature is maintained at 50° C. for the remainder of the 4.5 hours after which about 200 parts of sodium metabisulfite per million parts of monomers are added. The resultant viscous emulsion exhibits 99.28% conversion of monomers to polymer.

Stabilization of the polymer emulsion is accomplished by adding 1.57 grams of 30% NH₄OH slowly to the stirred emulsion at 40° C. to adjust the pH to 8.5. Stirring is continued for 0.5 hour.

To the resultant emulsion at 40° C. is added slowly an inverting agent over a period of 0.5 hour, 13.41 grams of surfactant consisting of 1 mole of nonyl phenol reacted with 9.5 moles of ethylene oxide. The resultant emulsion is held at 40° C. and stirred for an additional hour. The standard viscosity is 7.6 centipoises. The final polymer solids is 25.41%. A control run wherein the monomers are not treated gives 3.5 centipoises standard viscosity.

EXAMPLE 19

The procedure of Example 18, part A is repeated except 72 grams of acrylic acid alone is treated with 200 PPM NaBH₄ per million parts of monomer. For treatment the acrylic acid was adjusted to pH 10.0 with 30% aqueous NH₄OH while maintaining the temperature below 40° C.

After treatment and decomposition of excess NaBH₄, 45.5 grams of the treated acrylic acid is used in the preparation of an acrylamide copolymer aqueous phase using a pure chrystalline acrylamide.

The resulting homogenized emulsion has a viscosity of 958 centipoises and exhibits 98.66% conversion of monomer to polymer. The stabilized product emulsion with inverting agent has a standard viscosity of 6.7 centipoises. A control run wherein the acrylic acid is not treated with NaBH₄ gives 5.3 centipoises standard viscosity.

EXAMPLE 20

Following the procedures of Examples 16 and 18, a series of runs are made using two different sources of acrylamide. A first source C usually provides a pure acrylamide which is of satisfactory polymerizability and a second source D usually provides an acrylamide of inferior polymerizability. Samples from both of these sources are passed through an ion exchange column to remove cupric ion, treated with KBH₄, and used in the preparation of both solution and emulsion polymers. Control polymers are also prepared for reference. Details are as follows:

| Acrylamide Source | Treatment | | | | Emulsion STD. VIS. | Solution "As Is" STD. VIS. | Insolubles |
|---|---|---|---|---|---|---|---|
| | Type | ppm | pH | Time | | | |
| C | CONTROL | | | | 4.6 cps | 3.4 cps | 0.4% |
| C | KBH₄ | 200 | 10 | 2 hrs. | 4.6 | 3.5 | 0.1 |
| C | KBH₄ | 1000 | 10 | 2 hrs. | 4.8 | 3.6 | 0.0 |
| C | KBH₄ | 2000 | 10 | 2 hrs. | 4.9 | 3.5 | 0.4 |
| D | CONTROL | | | | 1.9 | 1.9 | 34.3 |
| D | KBH₄ | 200 | 10 | 2 hrs. | 2.4 | 2.9 | 19.3 |
| D | KBH₄ | 1000 | 10 | 2 hrs. | 2.6 | 3.6 | 7.1 |
| D | KBH₄ | 2000 | 10 | 2 hrs. | 2.7 | 3.6 | 3.0 |

The results show that the borohydride treatment has no adverse effect on an acrylamide of satisfactory polymerizability and improves the polymerizability of an acrylamide of interior polymerizability.

EXAMPLE 21

Following the procedure of Example 20, additional runs are made using the same two sources of acrylamide but using dimethylamine borane as the treating agent. Results are as follows:

| Acrylamide Source | Treatment | | | Emulsion Std. Vis. | Solution "As Is" Std. Vis. | Insolubles |
|---|---|---|---|---|---|---|
| | ppm | pH | Time | | | |
| C | CONTROL | | | 4.6 cps | 3.4 cps | 0.4% |
| C | 2000 | 5 | 2 hrs. | 3.5¹ | 2.7 | 0.2 |
| C | 2000 | 7 | 2 hrs | 3.6¹ | 2.8 | 0.1 |
| C | 2000 | 9 | 2 hrs. | 3.4 | 2.8 | 0.1 |
| D | CONTROL | | | 1.9 | 1.9 | 34.3 |
| D | 2000 | 5 | 2 hrs. | —² | 2.7 | 0.1 |
| D | 2000 | 7 | 2 hrs. | 3.8 | 2.8 | 0.2 |
| D | 2000 | 9 | 2 hrs. | —² | 2.8 | 0.1 |

NOTES:
DECOMPOSITION OF THE BORANE COMPOUND PRIOR TO POLYMERIZATION APPARENTLY IS NOT COMPLETE BECAUSE pH IS NOT TAKEN DOWN TO BELOW 3.
¹STRONG PREMATURE POLYMERIZATION
²MONOMER POLYMERIZED ON STANDING

EXAMPLE 22

The procedure of Example 20 is again repeated with the variation noted below. Again dimethylborane is used as treating agent.

| Acrylamide Source | Treatment | | | Emulsion Std. Vis. | Solution "As Is" Std. Vis. | Insolubles |
|---|---|---|---|---|---|---|
| | ppm | pH | Time | | | |
| C | CONTROL | | | 4.6 | 3.4 cps | 0.4% |
| C | 200 | 8.5 | 2 hrs. | 4.9 | 3.7 | 2.3 |
| C | 200 | 8.5 | 70 | 4.4 | 3.7 | 3.7 |
| C | 500 | 8.5 | 70 | 4.5 | 3.6 | 0.2 |
| D | CONTROL | | | 1.9 | 1.9 | 34.3 |
| D | 200 | 8.5 | 2 hrs. | 2.7 | 3.5 | 10.7 |
| D | 200 | 8.5 | 65 | 2.4 | 2.9 | 21.2 |
| D | 500 | 8.5 | 65 | 3.0 | 3.6 | 0.9 |

EXAMPLE 23

Following the procedure of Example 20 monoethylamine borane is employed as the treating agent. Results are as follows:

| Acrylamide Source | Treatment ppm | pH | Time | Emulsion Std. Vis. | Solution "As Is" Std. Vis. | Insolubles |
|---|---|---|---|---|---|---|
| C | CONTROL | | | 4.6 cps | 3.4 cps | 0.4% |
| C | 200 | 8.5 | 2 hrs. | 4.6 | 3.6 | 0.1 |
| C | 200 | 8.5 | 71 | 4.5 | 3.1 | 0.5 |
| C | 500 | 8.5 | 71 | 3.9 | 3.1 | 0.2 |
| D | CONTROL | | | 1.9 | 1.9 | 34.3 |
| D | 200 | 8.5 | 2 | 3.3 | 3.0 | 12.0 |
| D | 200 | 8.5 | 70 | 3.4 | 3.4 | 4.9 |
| D | 500 | 8.5 | 70 | 4.2 | 3.7 | 0.1 |

EXAMPLE 24

The procedure of Example 20 is again followed using monoisopropylamine borane as treating agents. Results are:

| Acrylamide Source | Treatment ppm | pH | Time | Emulsion Std. Vis. | Solution "As Is" Std. Vis. | Insolubles |
|---|---|---|---|---|---|---|
| C | CONTROL | | | 4.6 cps | 3.4 cps | 0.4% |
| C | 100 | 8.5 | 70 hrs. | 4.5 | — | — |
| C | 200 | 8.5 | 2 | 4.2 | 3.2 | 0.4 |
| C | 200 | 8.5 | 70 | 5.1 | 3.7 | 0.0 |
| C | 200 | 8.5 | 70 | 4.6 | — | — |
| C | 300 | 8.5 | 70 | 4.7 | — | — |
| C | 500 | 8.5 | 70 | 4.5 | 3.5 | 0.1 |
| D | CONTROL | | | 1.9 | 1.9 | 34.3 |
| D | 200 | 8.5 | 2 | 2.7 | 1.7 | 47.9 |
| D | 200 | 8.5 | 70 | 3.0 | 3.3 | 6.4 |
| D | 500 | 8.5 | 70 | 4.5 | 3.9 | 0.9 |

EXAMPLE 25

The procedure of example 20 is again followed using 2,6-lutidine borane as treating agent. Results are as follows:

| Acrylamide Source | Treatment ppm | pH | Time | Emulsion Std. Vis. | Solution "As Is" Std. Vis. | Insolubles |
|---|---|---|---|---|---|---|
| C | CONTROL | | | 4.6 cps | 3.4 cps | 0.4% |
| C | 25 | 8.0 | 70 Hrs. | — | 3.1 | 0.1 |
| C | 50 | 8.0 | 70 | — | 2.6 | 0.1 |
| C | 100 | 8.0 | 70 | — | 2.2 | 0.4 |
| C | 200 | 8.0 | 2 | 3.3 | 3.3 | 0.1 |
| C | 200 | 8.0 | 70 | 3.4 | 2.9 | 0.1 |
| C | 500 | 8.0 | 70 | 2.3 | 2.5 | 0.1 |
| D | CONTROL | | | 1.9 | 1.9 | 34.3 |
| D | 200 | 8.0 | 2 | 2.3 | 2.3 | 24.1 |
| D | 200 | 8.0 | 70 | 2.2 | 3.0 | 6.1 |
| D | 500 | 8.0 | 70 | 2.6 | 2.7 | 0.1 |

EXAMPLE 26

Following the procedures of Example 16 and 18, additional runs are made using NaBH₄ supported on silica or alumina as the treating agent using 5% based on the acrylamide. Results are:

| Acrylamide Source | Treatment pH | Time | Support | Solution "As Is" Std. Vis. | Insolubles |
|---|---|---|---|---|---|
| D | CONTROL | | — | 1.9 cps | 34.3% |
| D | 10 | 20 Hrs. | SiO$_2$ | 2.9 | 0.1 |
| D | 10 | 20 | Al$_2$O$_3$ | 3.0 | |

EXAMPLE 27

A series of acrylic acid homopolymers are prepared following the procedure of Example 16 except that no acrylamide is employed and the emulsion polymer solids are varied. Two commercially available monomer sources are used designated E and F. Variations in treatment and polymer viscosities are indicated in the following:

| Acrylic Acid Source | Type | Treatment ppm | pH | Time | Polymer Solids | Std. Vis. cps |
|---|---|---|---|---|---|---|
| E | CONTROL | | | | 30% | 6.3 |
| E | Amborane 345 | 2.5% | as is | 22 Hrs. | 30 | 6.4 |
| E | Amborane 355 | 2.5% | as is | 22 hrs. | 30 | 6.3 |
| E | CONTROL | | | | 30 | 6.6 |
| E | Amborane 345 | (1) | as is | (1) | 30 | 6.0 |
| E | Amborane 355 | (1) | as is | (1) | 30 | 5.6 |
| E | CONTROL | | | | 23 | 3.4 |
| E | NaBH$_4$ | 500 | 10 | 2 hrs. | 23 | 3.6 |
| E | NaBH$_4$ | 1000 | 10 | 2 | 23 | 3.8 |
| E | CONTROL | | | | 27 | 5.8 |
| E | CONTROL | | | | 30 | 5.6 |
| E | Monoisoproyl-amine borane | 200 | 7 | 70 | 30 | 6.0 |
| E | Monoisoproyl-amine borane | 500 | 7 | 70 | 30 | 5.7 |
| E | Monoisoproyl-amine borane | 1000 | 7 | 70 | 30 | 6.4 |
| E | Monoisoproyl-amine borane | 2000 | 7 | 70 | 30 | 6.0 |
| F | CONTROL | | | | 30 | 4.8(5.5)[2] |
| F | Amborane 345 | (1) | 7 | (1) | 30 | 5.2(5.9)[2] |
| F | Amborane 355 | (1) | 7 | (1) | 30 | 4.5(5.4)[2] |
| F | CONTROL | | | | 30 | 6.0 |
| F | Monoisopropyl-amine Borane | 1000 | 7 | 70 | | 7.1 |

Notes:
[1] Column treated, flow rate 50 ml/hr.
[2] Emulsion aged 81 days

EXAMPLE 28

Using an acrylamide source that when polymerized by the solution procedure of Example 3 gives a standard "as is" viscosity of 2.0 centipoises and 36.4% insolubles, treatment of the acrylamide with NaBH$_4$ is conducted in continuous fashion. Acrylamide solution and sodium borohydride solution are metered into a first vessel at rates which provide 340 parts of sodium borohydride per million parts of acrylamide and provide an average residence time of 170 minutes in the first vessel. The solution at pH 12 is stirred and sparged with air at the rate of 0.1 volume per volume of solution per minute while in the first vessel.

The overflow from the first vessel flows into a second vessel at a rate which provides an average resistance time of 170 minutes. Stirring and air sparging are as in the first vessel.

The overflow from the second vessel flows into a third vessel into which there is continuously added 85% phosphoric acid to maintain the pH at 4–5. Stirring is maintained and air is sparged at 0.25 volume per volume of solution per minute. Average residence time in the third vessel is 70 minutes.

When the product is polymerized by the process of Example 3, the resulting dried product shows a standard "as is" viscosity of 3.6 centipoises and insolubles of 0.4%.

What is claimed is:

1. A composition comprising:
   (a) a monomer of inferior polymerizability selected from acrylamide, acrylic acid and mixtures thereof, said monomer being in the form of a 10 to 60 weight percent aqueous solution having a pH above 8.0, said monomer containing an amount of oxygen such that said monomer solution has a positive oxygen solubility, and
   (b) a monomer-improving amount, insufficient to catalyze polymerization of said monomer, of an alkali metal borohydride.

2. The composition of claim 1 wherein said monomer contains a metallic ion or compound which can form an initiator system in the presence of the borohydride compound.

3. The composition of claim 1 wherein said borohydride compound is present in an amount of about 50 parts per million to about 2000 parts per million based on the monomer.

4. The composition of claim 1 further containing at least one additional ethylenically-unsaturated monomer capable of being copolymerized therewith to form a water-soluble copolymer.

5. The composition of claim 4 wherein said additional monomer is selected from the group consisting of acrylic acid or a salt thereof, 3-(methacrylamido)-propyltrimethyl ammonium chloride, dimethylaminoethylmethacrylate methyl sulfate quaternary salt and acrylonitrile.

6. The composition of claim 1 wherein said monomer is acrylamide.

7. The composition of claim 1 wherein said monomer is acrylic acid or a salt thereof.

8. The composition of claim 2 wherein said metallic ion is cupric.

9. The composition of claim 1 wherein said oxygen is provided by means of an air sparge.

10. The composition of claim 1 wherein said oxygen is present in at least 0.1 part per million based on the monomer.

11. The composition of claim 1 wherein said oxygen is present in at least 1 part per million based on the monomer.

12. The composition of claims 1, 2, 3, 4, 5, 6, 7, 8, 9, 10, or 11 wherein the borohydride compound is sodium borohydride.

* * * * *